United States Patent
Iwamoto et al.

(10) Patent No.: US 6,291,644 B1
(45) Date of Patent: Sep. 18, 2001

(54) PROTEIN, ITS GENE, REAGENTS FOR INDUCING APOPTOSIS, AND ANTICANCER AGENTS

(75) Inventors: Mitsunori Iwamoto, Karatsu; Sang-Kee Jung, Kyoto, both of (JP)

(73) Assignee: Tensei Suisan Co., Ltd., Saga-Lem (JP)

( * ) Notice: Subject to any disclaimer, the term of this patent is extended or adjusted under 35 U.S.C. 154(b) by 0 days.

(21) Appl. No.: 09/230,388

(22) PCT Filed: May 22, 1998

(86) PCT No.: PCT/JP98/02261

§ 371 Date: Jan. 22, 1999

§ 102(e) Date: Jan. 22, 1999

(87) PCT Pub. No.: WO98/52972

PCT Pub. Date: Nov. 26, 1998

(30) Foreign Application Priority Data

May 23, 1997 (JP) ................................................. . 9-133549

(51) Int. Cl.⁷ .............................. C07K 14/00; C07K 5/00; C07H 21/04
(52) U.S. Cl. .......................... 530/350; 530/326; 530/327; 530/328; 530/300; 536/23.11
(58) Field of Search .......................... 536/23.1; 530/326, 530/327, 328, 350

(56) References Cited

U.S. PATENT DOCUMENTS

5,266,683 * 11/1993 Oppermann et al. ................. 530/326
5,428,147 * 6/1995 Barker et al. ....................... 536/24.1

OTHER PUBLICATIONS

Soutschek J. et al. Apoptosis in the cerebellum of adult teleost fish, *Apteronotus leptorhynchus*, G.K.H. Zupanc/Developmental Brain Research 97 (1996), vol. 97 No. 2, pp. 279–286.

Andrews, PW et al, Inhibition of proliferation and induction of differentiation of pluripotent human embryonal carcinoma cells by osteogenic protein–1 (or bone morphogenetic protein–7)., Laboratory Investigation, 1994, 71/2, pp. 243–251.*

* cited by examiner

*Primary Examiner*—John S. Brusca
*Assistant Examiner*—Young Kim
(74) *Attorney, Agent, or Firm*—Darby & Darby

(57) ABSTRACT

Novel proteins which have cell death inducing activity or proliferation inhibitory activity on cancer cells; fragments of such proteins; genes coding such proteins; monoclonal antibodies to such proteins; reagents which induce apoptosis on cells including cancer cells in vitro for investigation of the mechanism of cell death induction, and which are obtained from the proteins including the amino acid sequence of SEQ ID No. 1 of the sequence listing, fragments thereof, genes coding these; and carcinostatic agents.

6 Claims, 7 Drawing Sheets

(A)

(B)

(C)

(D)

(A)

(B)

(C)

(D)

PROTEIN, ITS GENE, REAGENTS FOR INDUCING APOPTOSIS, AND ANTICANCER AGENTS

FIELD OF ART

The present invention relates to novel proteins which induce death of cancer cells by inducing apoptosis of the cells, or which exhibit cancer cell growth inhibitory activity, genes of such proteins, monoclonal antibodies to such proteins, reagents for qualifying cancer cell apoptosis, and carcinostatic agents.

PRIOR ART

Remarkable development in chemotherapy has been improving survival rate and remedial rate of patients having neoplastic diseases. On the other hand, however, strong side effects of carcinostatic agents give serious damage on normal cells, which has been recognized as a social problem. For prevention of side effects of carcinostatic agents, agents are demanded which have excellent selectivity for cancer cells or which are capable of controlling proliferation of oncocytes.

In conventional chemotherapy for cancer, administration dosage of agents is kept as low as possible since even the treatment dosage may cause harmful effects. Thus, attempts have been made to seek for potentiation by combination of a plurality of carcinostatic agents with different mechanisms of actions, or to improve carcinostatic effect by combination of a carcinostatic agent with other substances. In the latter case, a carcinostatic agent is usually combined with an immune activator to combine the direct effect on oncocytes with antineoplastic effect obtained through activation of immunocompetence of organism. Further, in some cases, radiotherapy or surgical treatment is performed in addition to these methods to improve the effect of the treatment.

Recently, it has been revealed that there are two different types of cell death, i.e., apoptosis (cell death governed by genes) and necrosis (cell death not governed by genes). Apoptosis and necrosis are usually distinguished by observing DNA fragmentation through biochemical measurement. This measurement shows that conventional carcinostatic agents exhibit carcinostatic effect by inducing necrosis of oncocytes, so that they cannot genetically control the death of oncocytes. On the contrary, active researches have been made on substances which induce apoptosis of oncocytes since such substances have possibility to control the death of oncocytes. Combination of an apoptosis-inducing carcinostatic agent with a conventional carcinostatic agent having different mechanism of action is expected to improve antineoplastic effect.

DISCLOSURE OF THE INVENTION

It is an object of the present invention to provide novel proteins which induce death of cells, in particular human cancer cells, by inducing apoptosis of the cells, or which exhibits cancer cell growth inhibitory activity; fragments of such proteins; genes of such proteins; and monoclonal antibodies to such protein.

It is another object of the present invention to provide reagents for apoptosis induction which induce apoptosis of cells, in particular of cancer cells, in vitro for the study of mechanism of cell death induction.

It is still another object of the present invention to provide carcinostatic agents which have proliferation inhibitory effect on human cancer cells or which have death inducing effect on cancer cells.

The present inventors have conducted intensive researches on peptides or proteins which induce apoptosis of cancer cells for applying conventionally known apoptotic cell death to oncotherapy. As a result, the inventors have found that some proteins purified from mackerel's viscus have apoptosis-inducing activity not only on blood cancer cells but also on a variety of tumor cancer cells, then synthesized cDNA, using the mRNA isolated from mackerel's viscus, determined the DNA sequence of the obtained cDNA, and estimated the amino acid sequence thereof, thereby completing the present invention.

In sum, according to the present invention, there are provided proteins comprising the amino acid sequence of SEQ ID No. 1 of the attached sequence listing, or the amino acid sequence at least partly homologous or analogous to the sequence of SEQ ID No. 1, and having proliferation inhibitory activity on cancer cells or cell death inducing activity; and fragments of such proteins.

According to the present invention, there are also provided proteins which have the amino acid sequence homologous to the amino acid sequence of SEQ ID No. 1 of the attached sequence listing, and which have proliferation inhibitory activity on cancer cells or cell death inducing activity.

According to the present invention, there are also provided proteins comprising amino acids 61–89 and 497–514 of SEQ ID No.1 of the attached sequence listing, and having proliferation inhibitory activity on cancer cells or cell death inducing activity.

According to the present invention, there are further provided genes which code the aforementioned proteins or their fragments, and genes which code the aforementioned proteins or their fragments and which comprise the DNA sequence of SEQ ID No. 2 of the attached sequence listing or the DNA sequence at least partly homologous or analogous to that of SEQ ID No. 2.

According to the present invention, there are further provided monoclonal antibodies to the aforementioned proteins or their fragments.

According to the present invention, there are also provided reagents for qualifying apoptosis comprising at least one member selected from the group consisting of the aforementioned proteins, their fragments, and the monoclonal antibodies thereto.

According to the present invention, there are also provided carcinostatic agents comprising the aforementioned proteins and their fragments as active components.

DESCRIPTION OF THE INVENTION

Figure 1:
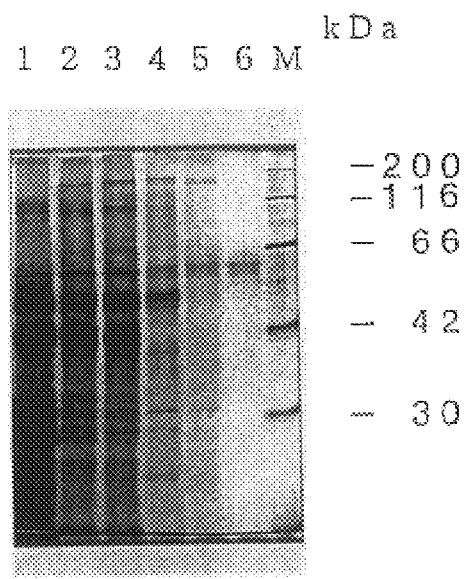
FIG. 1 is a photograph showing the results of silver-staining following SDS-PAGE of leukemia cell-killing active fractions prepared in Example 1, wherein Lane 1 shows the result of extract of mackerel's viscus, Lane 2 shows a fraction precipitated with ammonium sulfate, Lane 3 shows an active fraction obtained by gel filtration, Lane 4 shows a fraction adsorbed on Con A column, Lane 5 shows a fraction adsorbed on Mono Q, and Lane 6 shows final purified AIP (Apoptosis Inducing Protein).

The proteins and their fragments of the present invention are: (1) those including the amino acid sequence of SEQ ID No. 1 of the attached sequence listing; (2) those including an amino acid sequence at least partly homologous or analogous to the sequence of SEQ ID No. 1 and exhibiting proliferation inhibitory activity on cancer cells or cell death inducing activity; (3) those having the amino acid sequence homologous to the sequence of SEQ ID No. 1 of the sequence listing, and exhibiting proliferation inhibitory activity on cancer cells or cell death inducing activity; or (4) those including amino acids 61–89 and 497–514 of SEQ ID No. 1 of the attached sequence listing, and exhibiting proliferation inhibitory activity on cancer cells or cell death inducing activity.

In the present invention, "homologous to the sequence of SEQ ID No. 1" in above (2) means having preferably not lower than 70%, more preferably not lower than 90%, most preferably not lower than 95% homology to the sequence. A "sequence analogous to the amino acid sequence" means that the sequence is substantially homologous to the amino acid sequence of SEQ ID No. 1, and that the protein having such amino acid sequence has proliferation inhibitory activity on cancer cells or cell death inducing activity, similar to that exhibited by the proteins having the sequence of SEQ ID No. 1. Such amino acid sequence may be the sequence of SEQ ID No. 1 in which at least one amino acid is substituted; in which at least one new amino acid is inserted; or in which at least one amino acid is deleted.

In above (3), "having the amino acid sequence homologous to the sequence of SEQ ID No. 1" means that the sequence is recognized to be different from that of SEQ ID No. 1 only in a sequence portion varying depending on the species of the animal from which the protein derives, and that the protein has proliferation inhibitory activity on cancer cells or cell death inducing activity.

The proteins and their fragments of the present invention are believed to catalyze aldehyde-generating reaction by oxildative deamination shown below to cause generation of hydrogen peroxide, using ε-amino groups of proteins or amino acids, or amino groups of an amine compounds or amino acids as a substrate:

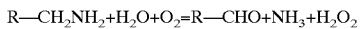

$$R—CH_2NH_2+H_2O+O_2=R—CHO+NH_3+H_2O_2$$

Further, the proteins and their fragments of the present invention are believed to require flavin as a coenzyme as one of the factors for exhibiting the proliferation inhibitory activity on cancer cells or the cell death inducing activity. Accordingly, it is preferred that the proteins and their fragments have amino acids 61–89 of the amino acid sequence of SEQ ID No. 1, which show the change similar to the typical change in absorption of the visible spectrum observed in flavoprotein. It is also preferred that the proteins and their fragments have amino acids 497–514 of the amino acid sequence of SEQ ID No. 1, which are believed to be essential for exhibiting cell death inducing activity.

In the proteins and their fragments of the present invention, "exhibiting cell death inducing activity" means to induce apoptosis, and this activity can be confirmed by such methods as observing DNA fragmentation, i.e., breakage of chromatin DNA into nucleosome units, by biochemical measurement; determining DNA fragmentation caused by apoptosis using flow cytometry; or directly detecting apoptosis by observation of morphological features under a microscope. The cells of which death is to be induced may include cancer cells, such as lung cancer, stomach cancer, colon cancer, ovarian cancer, brain tumor, mammary cancer, or renal cancer cells, adult T cell leukemia (ATL) cells, or cells infected with human T cell leukemia virus (HTLV-1).

The proteins and their fragments having homologous or analogous amino acid sequences to those of the present proteins and their fragments may easily be produced by conventional methods such as ordinary recombination technique.

Other structural features of the proteins and their fragments of the present invention are not particularly limited. For example, they may be modified, for example, with sugar chains.

The origin of the proteins and their fragments of the present invention is not particularly limited. For example, the protein having the sequence of SEQ ID No. 1 is isolated from viscus extract of mackerels infected with parasites. Thus, proteins and their fragments derived from mackerels (scientific name: Scomber japonicus, generic name: Chub mackerel) may be used. However, as will be discussed later in Examples, the proteins of the present invention are not obtained from viscus extracts of mackerels not infected with parasites. Therefore, the proteins are induced in mackerels by stimulation accompanied by activation of helper $T_2$ cells ($Th_2$ cells) such as parasite infection. Similarly, proteins similar to the proteins and their fragments of the present invention, or proteins and their fragments having amino acid sequences homologous to that of the present invention, may be induced also from mammals through the same mechanism. Accordingly, the proteins and their fragments of the present invention are not limited to those derived from mackerels, but may be those derived from mammals such as humans, mice, or rats. Such proteins derived from mammals have amino acid sequences which have homology to the sequence of SEQ ID No. 1 due to the difference in species.

The proteins having amino acid sequences homologous to that of SEQ ID No. 1 may easily be prepared, for example, from the genes cloned by hybridization using DNA containing the sequence of SEQ ID No. 2 with genes selected from a gene library of mammals.

The genes (DNA) of the present invention are those which code the proteins and their fragments mentioned above, and those which code the proteins and their fragments mentioned above and include the DNA sequence of SEQ ID No. 2 of the attached sequence listing or the DNA sequence at least partly homologous or analogous to that of SEQ ID No. 2. The "DNA sequence analogous to the sequence of SEQ ID No. 2" means that the genes have the DNA sequence of SEQ ID No. 2 in which at least one codon is substituted; in which at least one new codon is inserted; or in which at least one codon is deleted, and that the genes code the amino acids of the proteins of the present invention.

Such genes may be obtained by conventional methods, such as isolation from cDNA prepared by extracted mRNA, or isolation from genome DNA, or chemical synthesis.

The monoclonal antibodies of the present invention may be prepared by conventional methods, such as preparation of hybridoma using the proteins or their fragments as antigens.

The monoclonal antibodies of the present invention may be monoclonal antibody I38A (NATIONAL INSTITUTE OF BIOSCIENCE AND HUMAN TECHNOLOGY, AGENCY OF INDUSTRIAL SCIENCE AND TECHNOLOGY under International Deposit No. FERM BP-5872, deposited Mar. 13, 1997), monoclonal antibody I32D (NATIONAL INSTITUTE OF BIOSCIENCE AND HUMAN TECHNOLOGY, AGENCY OF INDUSTRIAL SCIENCE AND TECHNOLOGY, under International Deposit No. FERM BP-5873, deposited Mar. 13, 1997), or monoclonal antibody I310H (NATIONAL INSTITUTE OF BIOSCIENCE AND HUMAN TECHNOLOGY, AGENCY OF INDUSTRIAL SCIENCE AND TECHNOLOGY, under International Deposit No. FERM BP-5874, deposited Mar. 13, 1997).

The proteins and their fragments of the present invention may be obtained by constructing the aforementioned genes into appropriate expression vectors, delivering the vectors into host cells for transformation or transduction thereof, followed by proliferating the cells, and effecting intracellular or extracellular secretion of the target protein. The expression vectors to be used may be plasmids, viruses, and DNA fragments into which the genes of the present invention can be incorporated and which allow stable presence of the genes in the host cells to be expressed. The expression vectors require promoters, enhancer elements for controlling transcription, operator sequences, appropriate sequences of ribosome binding sites, sequences for controlling transcription and translation, and sequences for replicating vector DNA. For effecting extracellular secretion, secretory signal sequences are also required.

As the host cells, microorganisms, such as Escherichia coli or yeast, are useful. Also, COS7 cells derived from fibroblast of African green monkeys may be used. These may be commercially obtainable.

It is sufficient for the reagents for apoptosis induction of the present invention to contain at least one member selected from the group consisting of the proteins of the present invention, their fragments, and the monoclonal antibodies thereto of the present invention. The reagents are capable of inducing apoptosis of cells such as tumor cells, so that they may be used for kits to investigate the cell morphology, gene expression, and intracellular signal transduction mechanism of apoptotic cells.

The carcinostatic agents of the present invention contain the aforementioned proteins and/or their fragments of the present invention as active components, and optionally contain the monoclonal antibodies of the present invention, if required. The agents may be administered, for example, orally or by injection, and may be formed into, for example, powders, granules, tablets, capsules, liquid preparations, emulsions, or suspensions. The carcinostatic agents of the present invention may optionally contain pharmaceutically or galenical-pharmaceutically acceptable additives. Appropriate dosage may vary depending on the kind of cancers or other factors, but it is preferred to administer about 0.01–10 mg of active components per kilogram of patient's body weight per day.

The proteins and their fragments of the present invention are novel, have the activities to induce apoptosis of cells, in particular human cancer cells, to induce death of cancer cells or to inhibit proliferation of cancer cells, and are contained in edible fish such as mackerels. Thus, they are useful for functional foods for inhibiting cancer, carcinostatic agents, reagents for apoptosis induction, and the like. Further, the monoclonal antibodies of the present invention are useful for carcinostatic agents, reagents for apoptosis induction, and the like.

The genes of the present invention are capable of coding the proteins and their fragments of the present invention, so that they are useful for mass production of these.

The reagents for apoptosis induction induce apoptosis of cells, so that they are useful for investigating the cell morphology, gene expression, and intracellular signal transduction mechanism in apoptotic cells.

The carcinostatic agents of the present invention are capable of inducing apoptosis of cancer cells, so that they can control death of cancer cells to achieve carcinostatic effect, while they keep the side effects on other cells at an extremely low level.

EXAMPLES

The present invention will now be explained in detail with reference to Examples, but the present invention is not limited to these.

Example 1

Viscera were removed from mackerels, and homogenized in the equivalent weight of cold water. The homogenized mixture was centrifuged in a refrigerated centrifuge at 15000 G for 30 minutes to remove lipid and precipitate. The clear extract thus obtained was freezing-dried to obtain mackerel viscus dried powders. The viscus powders thus prepared were dissolved in distilled water at the concentration of 10 mg/ml, sufficiently cooled on ice, and saturated with 55% by weight ammonium sulfate. Then the saturated solution was centrifuged at 15000 rpm for 30 minutes to remove the precipitate, and the obtained supernatant was saturated with 95% by weight ammonium sulfate. The saturated solution was again centrifuged under the same conditions, and the precipitate was separated. To the precipitate thus obtained was added a small amount of Tris buffer (20 mM Tri-HCl, pH 7.5, 0.3M NaCl) to dissolve the precipitate, thereby obtaining a saturated fraction.

5 ml of the saturated fraction thus obtained as a sample was applied to a column (trade name "HiLoad 16/60 Superdex 200", manufactured by PHARMACIA FINE CHEMICALS CO.) which had been equilibrated with Tris buffer previously (to perform the gel filtration) at the flow rate of 60 ml/hour, and the active fraction was collected in aliquots of 2.5 ml each. The active fraction thus obtained was applied to a column (Con A-Sepharose column, manufactured by PHARMACIA FINE CHEMICALS CO.) which had been equilibrated with Tris buffer previously, and the column was washed with Tris buffer until the absorption at 280 nm was no longer observed.

The active fraction was eluted with Tris buffer containing 0.5M of methyl-α-D-mannopyranoside, dialyzed against bis-Tris buffer (20 mM bis-Tri-HCl pH 6.4, 100 mM NaCl), and concentrated by Ultrafree-15 (trade name "Biomax-50", manufactured by MILLIPORE Co.). The concentrate thus obtained was applied to a column (trade name "Mono Q 5/5 column, manufactured by PHARMACIA FINE CHEMICALS CO.) which had been equilibrated with bis-Tris buffer previously, and the column was washed with bis-Tris buffer until the absorption at 280 nm was no longer observed. Elution was performed with increasing concentrations of NaCl under the conditions below. The fraction containing the target peptides (proteins) was eluted at around 300 mM.

Conditions

Buffer A: 20 mM bis-Tris buffer, 100 mM NaCl, pH 6.4

Buffer B: 1M NaCl in Buffer A

Gradient: 0% B for 5 minutes, 0–50% B for 20 minutes, 50% B for 2 minutes, 50–100% for 5 minutes Flow Rate: 1.0 ml/min.

Detection: 280 nm, 0.2 AUFS

The active fraction thus obtained was concentrated by Ultrafree-15 (trade name "Biomax-50", manufactured by MILLIPORE CO., LTD.), and 1 ml of the sample was applied to a column (trade name "HiLoad 16/60 Superdex 200", manufactured by PHARMACIA FINE CHEMICALS CO.) which had been equilibrated with a phosphate buffer (trade name "Dulbecco PBS" manufactured by NISSUI PHARMACEUTICALS CO.) previously (to perform gel filtration) at the flow rate of 60 ml/hour, and the active fraction was collected in aliquots of 1 ml each, thereby purifying the target protein. Incidentally, the samples were centrifuged at 15000 rpm for 10 minutes and passed through a membrane filter with the pore size of 0.45 μm before each of the purification steps.

Purification of Human Leukemia Cell (HL-60) Killing Substance

Figure 2:
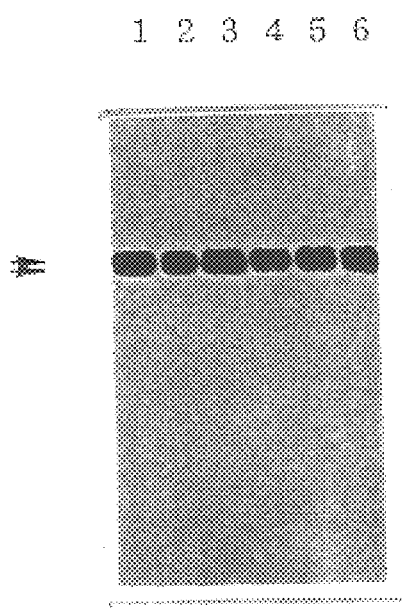
FIG. 2 is a photograph showing the results of immunostaining of leukemia cell-killing active fractions prepared in Example 1 with a monoclonal antibody to a leukemia cell-killing substance, following transferring of the fractions to PVDF membranes, wherein Lane 1 shows the result of extract of mackerel's viscus, Lane 2 shows a fraction precipitated with ammonium sulfate, Lane 3 shows an active fraction obtained by gel filtration, Lane 4 shows a fraction adsorbed on Con A column, Lane 5 shows a fraction adsorbed on Mono Q, and Lane 6 shows final purified AIP (apoptosis inducing protein).
Figure 3:
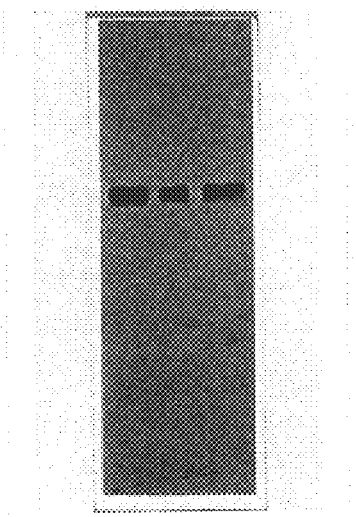
FIG. 3 is a photograph showing the results of Western blotting of extracts of mackerel's viscus prepared in Example 1 using each monoclonal antibody (I38A, I32D, and I310H) prepared in Example 2, wherein Lane 1 shows immunostaining with monoclonal antibody I38A, Lane 2 with monoclonal antibody I32D, and Lane 3 with monoclonal antibody I310H.

The leukemia cell-killing active fractions at each purification step were subjected to SDS-polyacrylamide gel electrophoresis (SDS-PAGE), followed by silver-staining or immunostaining with a monoclonal antibody to a leukemia cell-killing substance following transcription to a PVDF membrane. The results of the silver-staining were shown in FIG. 1, and the results of the immunostaining were shown in FIG. 2. As shown in Lane 6 in FIG. 1, the leukemia cell-killing substance purified by the above method exhibited bands only at about 62 and 63 kDa on SDS-PAGE. The proteins at 62 and 63 kDa were also detected by immunostaining using three independent monoclonal antibodies which are capable of completely absorbing the leukemia cell-killing activity by immunoprecipitation (FIG. 3). Further, the bands at 62 and 63 kDa having the leukemia cell-killing activity were cut out separately from PVDF membrane, and amino acid sequence of the N-terminal of each protein was determined. As a result, the sequence of the band at 62 kDa was found to be Glu His Leu Ala Asp Xaa Leu Glu Asp Lys Asp Tyr Asp Thr Leu Leu Gln Thr Leu Asp Asn Gly Leu Pro His Ile, and that of the band at 63 kDa was Glu His Leu Ala Asp Xaa Leu Glu Asp Lys Asp Tyr Asp Thr Leu Leu Gln Thr Leu Asp. Consequently, it was found that the amino acid sequences at N-terminals of the two proteins at 62 and 63 kDa were identical. This result gives possibility that the two proteins are the products from the same gene. This leukemia cell-killing substance was named "Apoptosis Inducing Protein (AIP)" for its apoptotic activity to be described later.

Example 2

Preparation of Monoclonal Antibodies to AIP

1) Immunization

10 μg of the purified AIP prepared in Example 1 was mixed with the equal volume of complete Freund's adjuvant, and subcutaneously injected to a five-week-old female BALB/c mouse. After two weeks, the equivalent amount of the antigen was mixed with the equal volume of incomplete Freund's adjuvant, and intraperitoneally injected into the same mouse. After three weeks, 30 μg of the antigen dissolved in a phosphate buffer solution (PBS) was intravenously injected to the mouse.

2)Fusion

Three days after boosting, splenic cells of the mouse and myeloma FOX-NY were fused in the presence of polyethylene glycol (PEG). The ratio of the splenic cells to the myeloma cells was 5:1. As a selective medium, 5% FBS-RPMI1640 containing AAT ($7.5 \times 10^{-5}$ M adenine, $8 \times 10^{-7}$M aminopterin, $1.6 \times 10^{-5}$M thymidine), insulin (10 mg/l), and transferring (10 mg/l) was used.

3) Cloning of Hybridoma

Immunoprecipitation was used for selecting antibody-producing hybridoma and for cloning. In the immunoprecipitation, 1 μl of AIP (40 μg/ml) was mixed with 20 μl of the supernatant of hybridoma culture, incubated at 4° C. for 2.0 hours, mixed with 3 g of anti-mouse IgG+IgM rabbit Igs, and further incubated for 1.0 hour. Subsequently, 50 μl of 10 % Staphylococcus aureus cell suspension (PANSORBIN Cells) was added to the reaction liquid, and the resulting mixture was incubated at 4° C. for 1.0 hour, and centrifuged at 10000 rpm for 2 minutes. 5 μl, 10 μl, and 20 μl each of the supernatant were taken out, and their apoptotic activity to human leukemia cells HL-60 were determined.

4) Preparation of Monoclonal Antibodies to Leukemia Cell-Killing Substance

At day 8 of the cell fusion, a total of 768 wells were screened by enzyme-linked immunosorbent assay (ELISA)

to select wells containing anti-AIP antibody, and 56 ELISA positive wells were obtained. At day 10 of the cell fusion, 56 ELISA positive wells were subjected to immunoprecipitation and Western blotting to select 9 wells which were positive in all of ELISA, immunoprecipitation, and Western blotting. Three out of the 9 wells which produced the largest number of antibodies were subjected to cloning by three cycles of limiting dilution-cloning method to obtain three independent clones. Each clone was named I38A (NATIONAL INSTITUTE OF BIOSCIENCE AND HUMAN TECHNOLOGY, AGENCY OF INDUSTRIAL SCIENCE AND TECHNOLOGY under International Deposit No. FERM BP-5872), I32D (NATIONAL INSTITUTE OF BIOSCIENCE AND HUMAN TECHNOLOGY, AGENCY OF INDUSTRIAL SCIENCE AND TECHNOLOGY, under International Deposit No. FERM BP-5873), and I310H (NATIONAL INSTITUTE OF BIOSCIENCE AND HUMAN TECHNOLOGY, AGENCY OF INDUSTRIAL SCIENCE AND TECHNOLOGY, under International Deposit No. FERM BP-5874), respectively. The results of Western blotting of the extract of mackerel's viscus using I38A, I32D, and I310 H are shown in FIG. 3. Isotypes of monoclonal antibodies I38A, I32D and I310H were determined by immunostaining using isotype specific anti-mouse antibodies. The results are shown in Table 1. Monoclonal antibodies I38A, I32D, and I310H were useful in all of ELISA, immunoprecipitation, and Western blotting.

TABLE 1

| Antibody | Class | ELISA | Immuno-precipitation | Immuno-staining |
| --- | --- | --- | --- | --- |
| I38A | IgG 1(k) | + | + | + |
| I32D | IgG 1(k) | + | + | + |
| I310H | IgG 1(k) | + | + | + |

+: usable

Example 3
Measurement of Apoptotic Activity of AIP

Myelomonocytic cell line HL-60 obtained from peripheral blood of a patient with acute promyelocytic leukemia was used as the cells. RPMI1640 medium (manufactured by MENEKI SEIBUTSU KENKYUSHO, IBL) with 10% fetal bovine serum (FBS) was used as medium. FBS has been heated at 56° C. for 45 minutes to inactivate the complement system before use.

First, the cell suspension was poured into a tube, centrifuged at 1000 rpm for 5 minutes to remove the supernatant, and then resuspended in an appropriate amount of 10% FBS RPMI1640. The number of cells was adjusted to be $5.0 \times 10^5$ cells/ml, and the suspension was treated with the purified AIP prepared in Example 1 which had been adjusted to various concentrations.

Cell death was measured by Cell Titer 96 (trade name "Aqueous Non-Radioactive Cell Proliferation Assay Kit" manufactured by PROMEGA CO.).

DNA fragmentation was determined by the following process. 250 μl of the cell suspension ($1.25 \times 10^5$ cells) was mixed with 62.5 μl of a lysis buffer (2.0M NaCl, 10 mM EDTA, 50 mM Tris-HCl, pH 8.0, 1% SDS) and 4 μl of protease K (20 mg/ml), and dissolved at 56° C. for 90 minutes. The resulting solution was left still on ice for 5 minutes, mixed with 80 μl of 5M NaCl, left on ice for another 5 minutes, and centrifuged at 12000 rpm for 5 minutes. To 400 μl of the supernatant thus obtained, 4 μl of RNaseA (20 mg/ml) was added, and the resulting mixture was treated at 37° C. for 60 minutes to digest RNA, then mixed with 900 μl of cold ethanol, and left till at −20° C. overnight. The resulting mixture was centrifuged at 15000 rpm for 20 minutes. The resulting precipitate was dissolved in 10 μl of TE buffer (10 mM Tris-HCl, pH 7.5, 1 mM EDTA), and subjected to analysis by 2% agarose gel electrophoresis. As a marker, 123 bp DNA ladder marker (LIFE TECHNOLOGIES) was used.

Detection of DNA breakage by measuring DNA content was carried out as follows. $1 \times 10^6$ cells of HL-60 which had been treated with 20 ng/ml of AIP for a predetermined period of time to induce apoptosis were washed with PBS (−), mixed with 200 μl of 70% cold ethanol, and fixed at 4° C. overnight. The mixture was centrifuged at 1500 rpm for 5 minutes, the supernatant was removed, and the cells were washed with PBS(−) for removing ethanol. The obtained cell pellet was suspended in 0.1 ml of PBS(−), mixed with 2.5 μl of RNaseA (20 mg/ml), and treated at 37° C. for 20 minutes to digest RNA. After that, the cells were collected by centrifugation, mixed with 0.5 ml of a 50 μg/ml propidium iodide solution (0.1% sodium citrate, 0.1% NP-40) to effect staining at 4° C. for 10 minutes in dark, then passed through 50 μm nylon mesh, and subjected to a flow cytometry for determination.

Observation of chromatin condensation by fluorescent staining was carried out as follows. $1 \times 10^6$ cells of HL-60 which had been treated with 20 ng/ml of AIP for a predetermined period of time to induce apoptosis were washed with PBS(−), mixed with 100 μl of a cell fixing solution (PBS(−) containing 1% glutaraldehyde), and left still at room temperature for 30 minutes for fixing. The resulting mixture was centrifuged at 1500 rpm for 5 minutes to remove the supernatant, and washed with PBS(−). The resulting cell pellet was suspended in 20 μl of PBS(−), and mixed with 4 μl of 1 mM HOECHST 33258 in PBS(−). A drop of the cell suspension was put on a slide glass, covered with a cover glass, and observed under a fluorescence microscope.

Carcinostatic effect was tested using cultured human cancer cell panels in the following method. A total of 39 lines of cultured cancer cells consisting of 38 lines of cultured human cancer cells (7 lines of lung cancer, 6 lines of stomach cancer, 6 lines of colon cancer, 5 lines of ovarian cancer, 6 lines of brain tumor, 5 lines of mammary cancer, 2 lines of renal cancer, and 1 line of melanoma) and mouse P388 leukemia cells were spread over 96-well plates. On the next day, AIP at various concentrations was added to the wells, and after 48 hours, cell proliferation was determined by calorimetric assay with sulforhodamine B.

Effect of AIP on proliferation of adult T cell leukemia (ATL) cells and cells infected with human T cell leukemia virus-1 (HTLV-1) was examined in the following method.

$1 \times 10^5$ cells each of three lines of ATL cells (Maeda-V, Fukuda-V, Hara-V) and 2 lines of cells infected with human T cell leukemia virus-1 (HTLV-1) (OYAJ-V, YAM-V) were mixed with AIP so that the final concentration was 0, 2, and 22 ng/mg, respectively; cultured at 37° C. in 5% $CO_2$ for 7 hours; then mixed with 0.5 μCi 6-$^3$H thymidine; and cultured for 5 hours. The resulting cultures were washed three times with PBS (−), and the amount of 6-$^3$H thymidine taken up by DNA was determined by a liquid scintillation counter.

1) Apoptotic Activity of Leukemia Cell-Killing Substance

Figure 4:
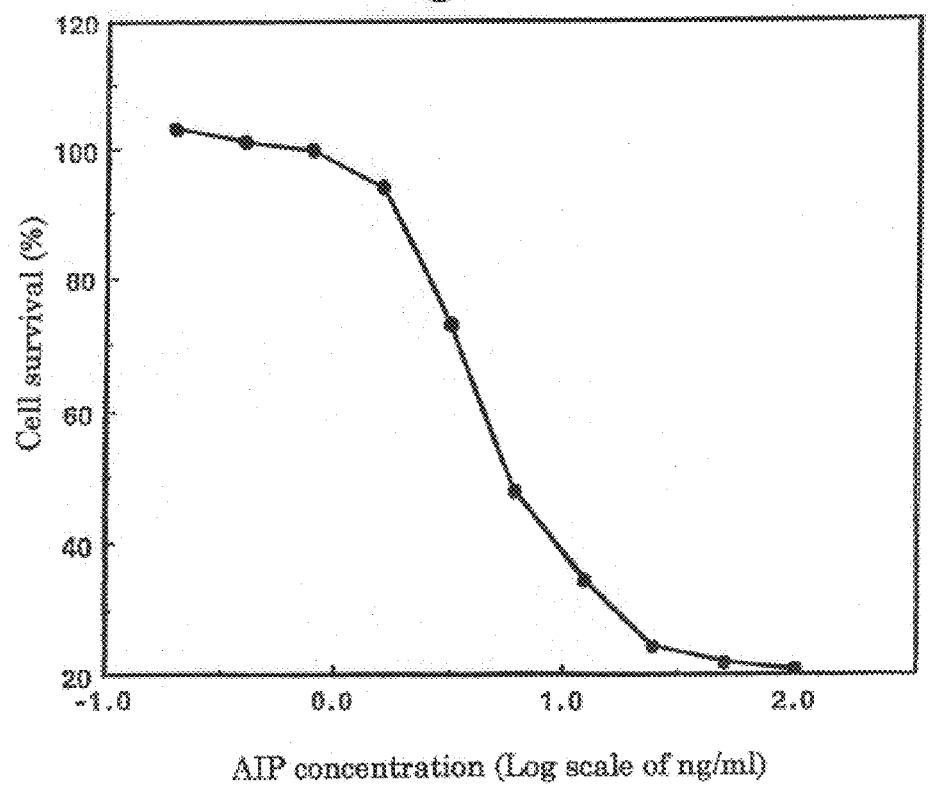
FIG. 4 is a graph showing the cell-killing activity of a purified leukemia cell-killing substance on human leukemia cell HL-60 confirmed in Example 3 by means of relationship between the concentration measured by MTS assay and the percentage of viable cells 16 hours after the treatment.
Figure 5:
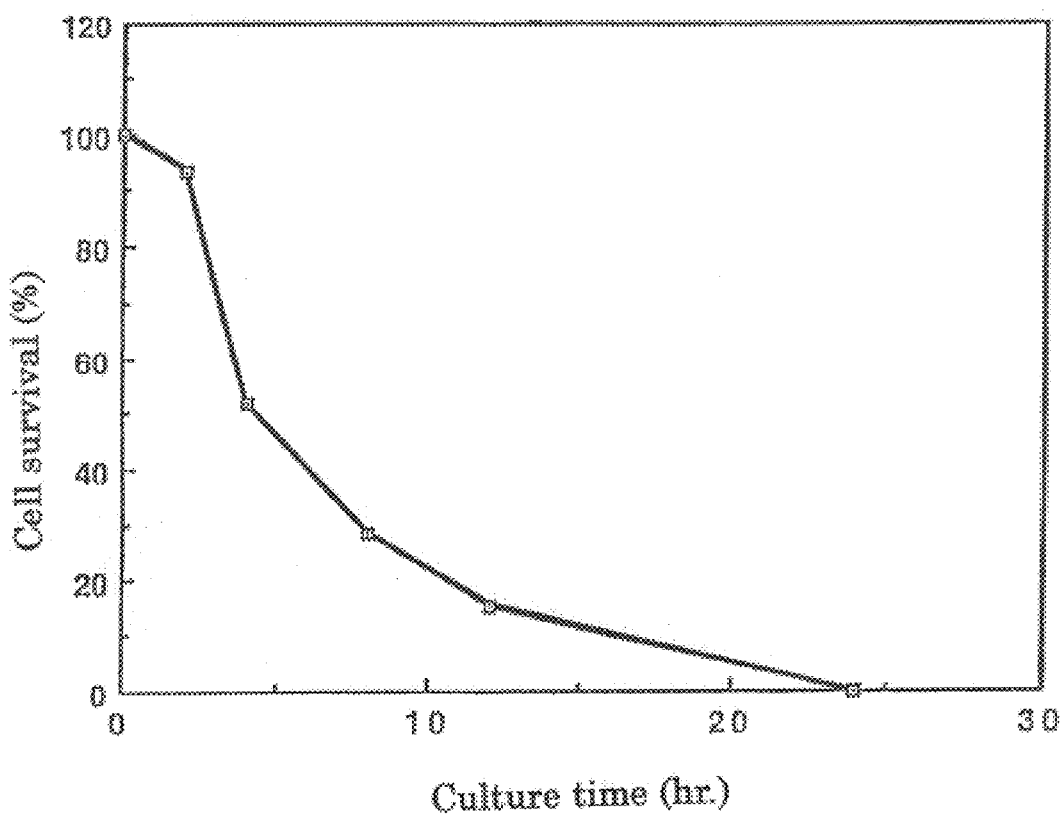
FIG. 5 is a graph showing the results of analysis in Example 3 in the percentage of the viable cells after treatment with a leukemia cell-killing substance taken with the lapse of time.
Figure 6:
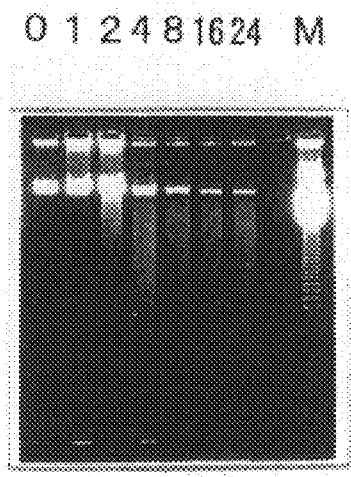
FIG. 6 is a photograph showing the DNA fragmentation after treatment with a leukemia cell-killing substance analyzed with the lapse of time in Example 3, wherein the number on each lane indicates the time lapsed in hours, and M indicates the 123 bp molecular size marker.
Figure 7:
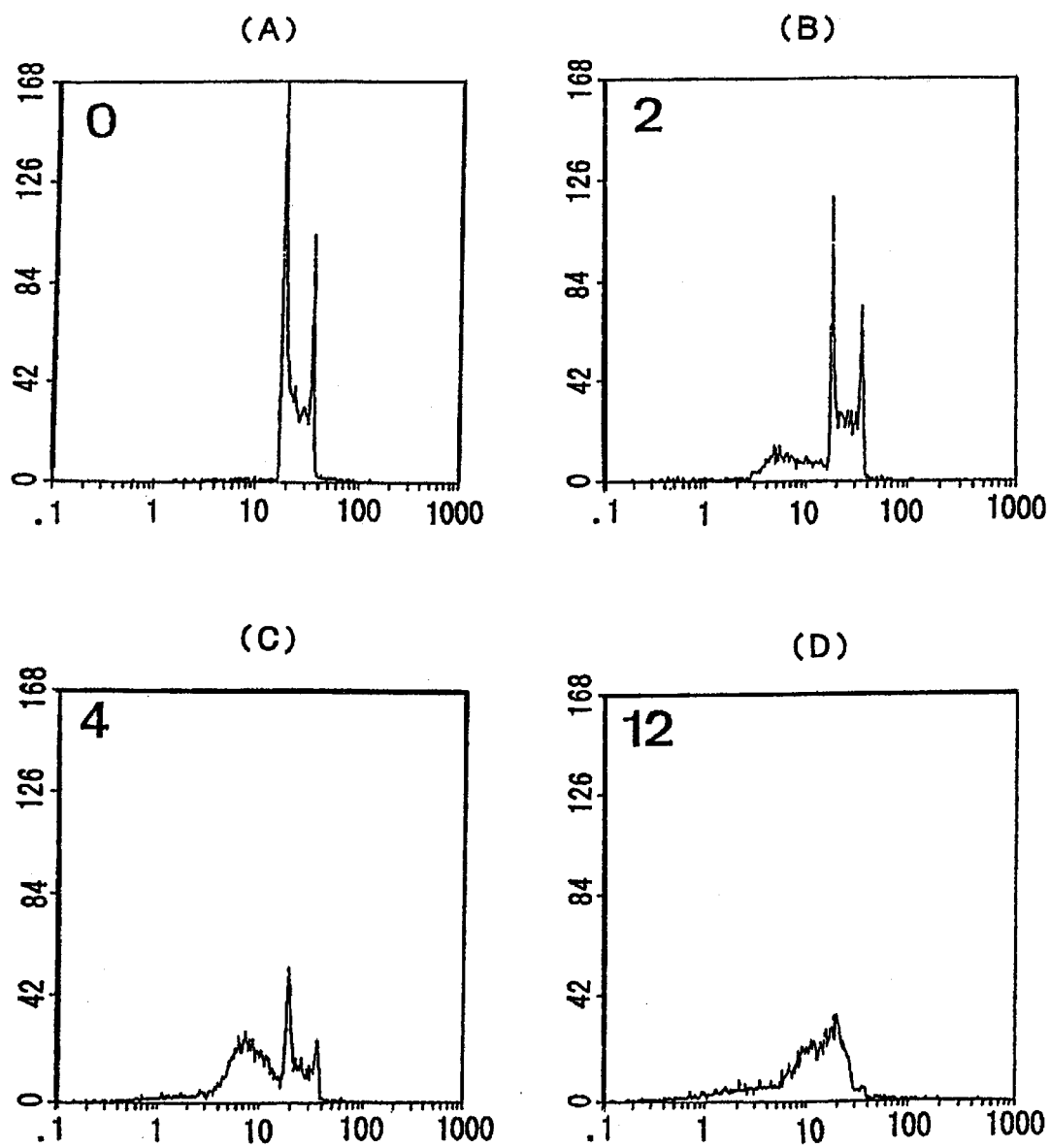
FIG. 7 illustrates graphs showing DNA contents of cells analyzed by flow cytometry 0 hour (FIG. 7(A)), 2 hours (FIG. 7(B)), 4 hours (FIG. 7(C)), and 12 hours (FIG. 7(D)) after the treatment with a leukemia cell-killing substance in Example 3, wherein the ordinate represents the cell count, and the abscissa represents the florescence intensity.

Killing activity of the purified leukemia cell-killing substance on human leukemia cell HL-60 was determined by MTS assay. The relationship between the concentration and the percentage of the viable cells 16 hours after the treatment is shown in FIG. 4. The substance at the concentration of about 5 ng/ml killed about 50% of $5 \times 10^5$ cells/ml, which indicated that the substance had a very strong leukemia cell-killing activity. The results of the analysis of the percentage of the viable cells with the lapse of time after treatment with the leukemia cell-killing substance at the concentration of 20 ng/ml are shown in FIG. 5. As a result, it was found that death of about 50% of the cells was induced in about 4 hours. The results of the analysis of DNA fragmentation with the lapse of time after treatment with the leukemia cell-killing substance at the concentration of 20 ng/ml are shown in FIG. 6. Two hours after the treatment, DNA fragmentation into nucleosome units was observed to start, which is specific in apoptosis. It is generally known that, in cell death by apoptosis, apoptosis-specific DNA fragmentation, i.e. breakage of chromatin DNA into nucleosome units, is observed.

The DNA fragmentation in apoptosis may also be determined by flow cytometry, wherein the apoptotic cells are detected as the cells having lower DNA content than those in G1 phase. The results of the analysis by flow cytometry of the DNA content of the cells 0, 2, 4, and 12 hours after the treatment with the leukemia cell-killing substance at the concentration of 20 ng/ml, respectively, are shown in FIGS. 7(A), 7(B), 7(C), and 7(D), respectively. As a result, it was observed that the apoptotic cells with lower DNA content increased with the lapse of time.

Figure 8:
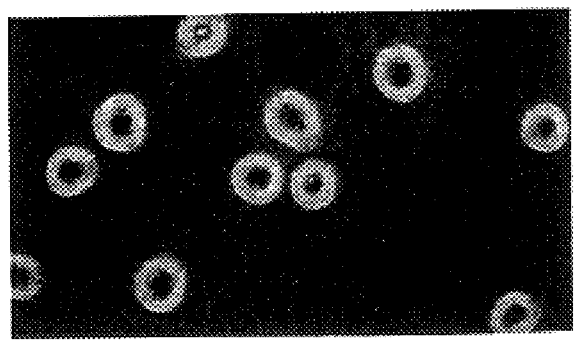
FIG. 8 shows microscopy photographs, showing morphological changes in cells treated with a leukemia cell-killing substance in Example 3, wherein (A) indicates the result 0 hour after the treatment, (B) indicates the result 2 hours after the treatment, (C) indicates the result 4 hours after the treatment, and (D) indicates the result 12 hours after the treatment.
Figure 8:
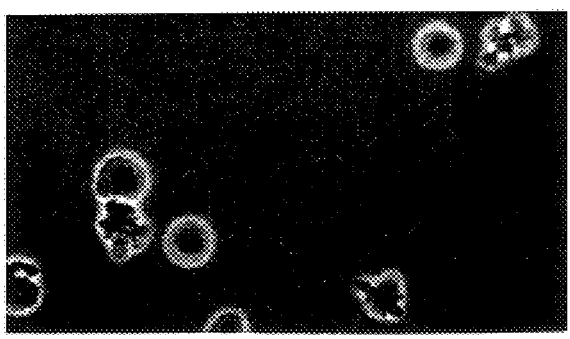
Figure 8:
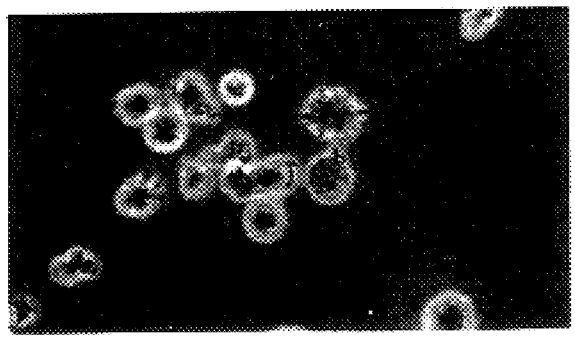
Figure 8:
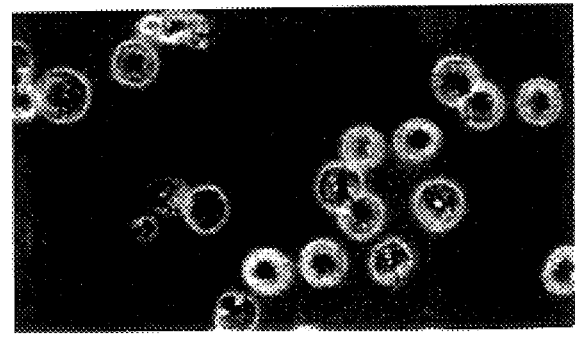
Figure 9:
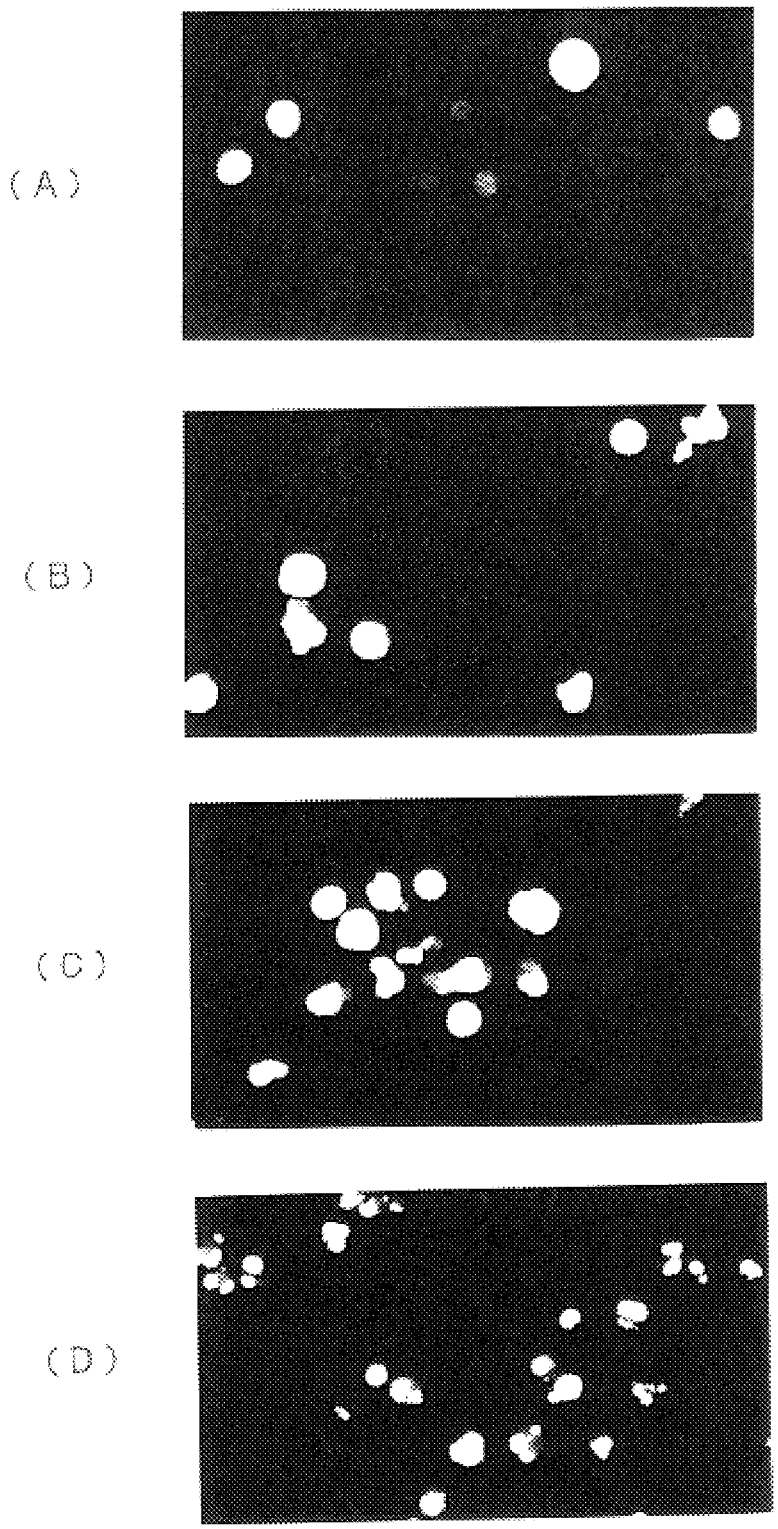
FIG. 9 shows fluorescence microscopy photographs, showing the results of fluorescent-staining with HOECHST 33258 of the nuclei of the cells treated with a leukemia cell-killing substance after the lapse of time as each shown in FIG. 8, wherein (A) indicates the result 0 hour after the treatment, (B) indicates the result 2 hours after the treatment, (C) indicates the result 4 hours after the treatment, and (D) indicates the result 12 hours after the treatment.

Apoptosis may also be detected directly under a microscope by the morphological features. Thus, morphological changes of the cells 0, 2, 4, and 12 hours after the treatment with the leukemia cell-killing substance at the concentration of 20 ng/ml, respectively, were observed under a microscope. The microscopy photographies are shown in FIGS. 8(A), 8(B), 8(C), and 8(D), respectively. In the nucleus of the apoptotic cells, chromatin condensation and nucleus fragmentation were observed. Further, the nucleus of the cells 0, 2, 4, and 12 hours after the treatment with the leukemia cell-killing substance at the concentration of 20 ng/ml, respectively, as shown in FIG. 8 were subjected to fluorescent staining with HOECHST 33258, and examined under a fluorescence microscope. The results are shown in FIGS. 9(A), 9(B) 9(C), and 9(D), respectively. As a result, chromatin condensation and/or fragmented nucleus image, which is specific for apoptosis, was determined in the cells treated with the leukemia cell-killing substance.

From the above results, it was decided that the cell death caused by the treatment with the leukemia cell-killing substance was apoptosis.

2) Proliferation Inhibitory Activity of AIP on Human Cancer Cells

Effect of AIP on proliferation of 43 kinds of human cancer cells was determined by calorimetric assay with sulforhodamine B or by uptake of 6-$^3$H thymidine. The results are shown in Table 2. It was confirmed that AIP inhibited proliferation of the cells examined.

TABLE 2

| Cell | Inhibition of Proliferation | Cell | Inhibition of Proliferation | Cell | Inhibition of Proliferation |
|---|---|---|---|---|---|
| HBC-4 | + | HCT-15 | + | RXF-631L | + |
| BSY-1 | + | HCT116 | + | St-4 | + |
| MCF-7 | + | NCl-H23 | + | MKN1 | + |
| MDA-MB-231 | + | NCl-H226 | + | MKN7 | + |
| U251 | + | NCl-H522 | + | MKN28 | + |
| SF-268 | + | NCl-H460 | + | MKN45 | + |
| SF-295 | + | DMS273 | + | MKN74 | + |

TABLE 2-continued

| Cell | Inhibition of Proliferation | Cell | Inhibition of Proliferation | Cell | Inhibition of Proliferation |
|---|---|---|---|---|---|
| SF-539 | + | DMS114 | + | HBC-5 | + |
| SNB-75 | + | LOX-IMVI | + | A549 | + |
| SNB-78 | + | OVCAR-3 | + | ACHN | + |
| HCC2998 | + | OVCAR-4 | + | OYAJ-V | + |
| KM-12 | + | OVCAR-5 | + | YAM-V | + |
| HT-29 | + | OVCAR-8 | + | Maeda-V | + |
| WiDr | + | SK-OV-3 | + | Fukuda-V | + |
|  |  |  |  | Hara-V | + |

Example 4

1) Isolation of Total RNAs from Mackerel's Viscus

Total RNAs were isolated in accordance with AGPC (Acid Guanidinium-Phenol-Chloroform) method (Anal. Biochem. 162, p156–159).

Viscus of mackerels were dissolved and homogenized in 5 ml of a solution consisting of phenol and guanidine thiocyanate, ISOGEN (manufactured by Kabushiki Kaisha Nippon Gene), using Polytoron homogenizer. To the homogenized solution thus obtained, 1 ml of chloroform was added, and thoroughly mixed with the contents. The resulting mixture was left on ice for 15 minutes, centrifuged at 4° C. at 5000 G for 30 minutes to collect the upper phase (aqueous phase). To this solution, equal volume of phenol/chloroform solution was added to extract the aqueous phase, to which isopropyl alcohol in the volume equal to the extracted aqueous phase was added, and the resulting mixture was left at room temperature for 10 minutes. The mixture was then centrifuged at 4° C. at 5000 G for 30 minutes to precipitate RNA, which was then washed with 70% ethanol. The RNA pellet was dissolved in 1 ml of an elution buffer (10 mM Tri-HCl, pH 7.4, 1 mM EDTA), thereby obtaining 1 mg of all the RNAs.

2) Preparation of mRNA

Total RNAs thus obtained were treated at 65° C. for 5 minutes, and rapidly quenched. The insolubles were removed by centrifugation, and 0.2 ml of 3M NaCl solution was added to the remaining to adjust the salt concentration to 0.5 M. The RNA solution was applied to an oligo(dT) cellulose column (manufactured by PHARMACIA FINE CHEMICALS CO.), and the fraction passed through the column was again applied to the column. The column was then washed with a solution of 10 mM Tri-HCl, pH 7.4, 1 mM EDTA, 0.5M NaCl (in an amount for several columns) and with a solution of 10 mM Tri-HCl, pH 7.4, 1 mM EDTA, 0.1M NaCl (in an amount for several columns), and the adsorbed RNA having poly(A) was eluted with an elusion buffer. The RNA thus obtained was subjected to another round of purification, mixed with $^1$/$_{10}$ volume of 3M sodium acetate (pH 5.1) and 2 volumes of ethanol, and precipitated at −20° C., thereby obtaining about 35 μg of mRNA having poly(A).

3) Synthesis of cDNA and Preparation of cDNA Library

3 μg of mRNA having poly (A) thus obtained was mixed with distilled water to increase the volume to 7 μl, mixed with 2 μl of Not 1 primer-adapter (0.5 μg/ml, LIFE TECHNOLOGIES), treated at 70° C. for 10 minutes, and then rapidly quenched. To the resulting solution, 1 μl of RNAse inhibitor (40 unit/μl, manufactured by STRATAGENE CO.), 4 μl of a buffer consisting of 250 mM Tri-HCl, pH 8.3, 375 mM KCl, and 15 mM MgCl$_2$, 1 μl of DTT, 1 μl of 10 mM dNTP mixture, and a reverse transcriptase (200 units/μl, LIFE TECHNOLOGIES) were added, thoroughly mixed, and reacted at 37° C. for 1 hour. After the reaction, 91 μl of distilled water, 30 μl of a buffer consisting of 100 mM Tris-HCl, pH 6.9, 450 mM KCl, 23 mM MqCl$_2$, 0.75 mM β-NAD+, and 50 mM (NH$_4$)$_2$SO$_4$, 3 μl of 10 mM dNTP mixture, 1 μl of E. coli DNA ligase (10 units/μl), 4 μl of E. coli DNA polymerase (10 units/μl) and 1 μl of E. coli RNaseH (2 units/μl) were added, thoroughly mixed, and reacted at 16° C. for 2 hours. After that, 2 μl of T4DNA polymerase (5 units/μl) was added, and further reacted for 5 minutes. 10 μl of 0.5M EDTA was added to the reaction mixture to terminate the reaction, and subjected to extraction with phenol-chloroform (1:1). The extracted upper aqueous phase was mixed with 0.5 volume of 7.5M ammonium acetate and two volumes of ethanol. The resulting mixture was centrifuged at 14000 G for 20 minutes, and the separated pellet was carefully rinsed with 70% ethanol. After drying, the pellet was dissolved in 25 μl of distilled water, to which 10 μl of a buffer consisting of 250 mM Tri-HCl, pH 7.6, 50 mM MgCl$_2$, 5 mM ATP, 5 mM DTT, and 25% (w/v) PEG8000, 10 μl of Sal 1 adapter (1 μg/μl), and 5 μl of T4DNA ligase (1 unit/μl) were added, and reacted at 16° C. for 24 hours. The resulting reaction product was subjected to extraction with phenol-chloroform (1:1), followed by precipitation with ethanol. The resulting precipitate was dissolved in 41 μl of distilled water, to which 5 μl of a buffer consisting of 10 mM Tri-HCl, pH 7.5, 7 mM MgCl$_2$, 150 mM NaCl, 7 mM 2-mercaptoethanol, and 0.01% TritonX-100, and 4 μl of NotI (15 units/μl) were added, and reacted at 37° C. for 2 hours. The resulting reaction product was subjected to extraction with phenol-chloroform (1:1), followed by precipitation with ethanol. The obtained DNA pellet was dissolved in 100 μl of a buffer consisting of 10 mM Tri-HCl, pH 7.5, 0.1 mM EDTA and 25 mM NaCl, and the solution thus obtained was subjected to gel filtration through Sephacryl S-500 column (1 ml, LIFE TECHNOLOGIES) which had been equilibrated with the same buffer, thereby selecting the fraction containing cDNA of the required size.

A mixture of 15 ng of the cDNA thus prepared and 50 ng of pSPORT 1 plasmid vector (LIFE TECHNOLOGIES) which had been treated with Not I-Sal I was mixed with distilled water to bring the volume to 15 μl, to which 4 μl of a buffer consisting of 250 mM Tri-HCl, pH 7.6, 50 mM MgCl$_2$, 5 mM ATP, 5 mM DTT, and 25% (w/v) PEG8000, and 1 μl of T4DNA ligase (1 unit/μl) were added, and reacted at 22° C. for 4 hours to ligate cDNA into the vector. 5 μl of yeast tRNA (1 μg/μl), 12.5 μl of 7.5M NH$_4$OAc, and 70 μl of cold ethanol were added to effect ethanol-precipitation, and the resulting precipitate was dissolved in 5 μl of distilled water. The vector cDNA thus obtained was transformed into E. coli cells for electroporation (Electro MAX DH10B Cell) using an electroporation system manufactured by BIORAT CO. (1.8 kV, 25 mF, 200Ω), thereby obtaining a cDNA library of 2,300,000 transformants.

4) Amplification of AIP Genes by RT-PCR (Reverse Transcription Polymerase Chain Reaction)

Sense primer No. 1 corresponding to EDKDYDT of the amino acid sequence in the N-terminal of AIP (EHLADXLEDKDYDTLLQTLDNGLPHI) and antisense primer No. 2 corresponding to MIYDQAD in the internal amino acid sequence (MIYDQADV) were chemically synthesized, respectively, and used as amplification primers for AIP genes. To 5 μg of all the RNAs obtained above, 1 μl of oligo(dT)$_{12-18}$ (0.5 ng/μl) was added, and the resulting mixture was incubated at 75° C. for 10 minutes, and rapidly quenched in ice. Then cDNA synthesis reaction was effected at 42° C. for 1 hour in a solution containing 20 mM Tris-HCl (pH 8.4), 50 mM KCl, 2.5 mM MgCl2, 0.5 mM each of dNTP, 10 nM DTT, 20 units RNAse inhibitor, and 200 units of reverse transcriptase. The reaction system was then heated at 70° C. for 10 minutes to terminate the reaction. 2 units of E. coli RNaseH was added and treated at 37° C. for 20 minutes, thereby digesting the remaining RNA. In a solution containing ⅒ amount of the obtained cDNA, 100 pmole each of the two kinds of primers Nos. 1 and 2, 20 mM Tris-HCl (pH 8.4), 50 mM KCl, 1.5 mM MgCl$_2$, 0.2 mM each of dNTP, 10 mM DTT, and 2.5 units of Taq DNA polymerase, PCR was performed by repeating 35 cycles of reactions at 94° C. for 1 minute, 56° C. for 1 minute, and 72° C. for 1 minute. After the completion of these cycles, another reaction was effected at 72° C. for 8 minutes, so that poly(A) was incorporated at the 3' terminal of the PCR product.

5) Cloning of PCR Product and Determination of DNA Sequence Thereof

It was confirmed by 2% agarose gel electrophoresis that the PCR product thus obtained was about 650 bp in size. The PCR product was inserted into plasmid vector pCRII using T4DNA ligase and ATP, and the DNA sequence was determined by a dye terminator method by fluorescent-labeling of dideoxy nucleotide in accordance with the instructions for a kit manufactured by PERKIN ELMER CO. (ABI PRISM Dye Terminator Cycle Sequencing Ready Reaction Kit). As a result, the amino acid sequence estimated from the DNA sequence was found to include a sequence obtained by determination of a partial amino acid sequence of AIP, and name pCRaip001.

6) Labeling of Probe pCRaip001 thus obtained was cleaved with restriction enzyme Eco RI, separated by 1.5% agarose gel electrophoresis, and insert DNA fragments of about 650 bp were eluted from the agarose gel. 60 ng of the purified DNA fragments were prepared into a template, and labeled with [α-$^{32}$P]dCTP by random primer method in accordance with the instructions for a kit manufactured by PHARMACIA FINE CHEMICALS CO. (Ready To Go DNA Labeling Kit).

7) Screening of Complete AIP Genes from pSPORT 1 cDNA Library pSPORT 1 cDNA Library prepared above was subjected to screening by colony hybridizationmethod (Proc. Natl. Acad. Sci. U.S.A. 72: 3961, 1975) using the probe obtained above. First, about 1,000,000 cells of the transformants obtained above were spread over a 15 cm LB/ager plate containing ampicillin so that about 20000 colonies were formed, and cultured at 37° C. for 12 hours. Over the plate on which the colonies had been formed, a nylon filter (manufactured by AMERSHAM CO.) was placed so that no air was captured therebetween. After 1 minute, the filter was peeled off and dried. The filter with the side having the colonies up was placed on a filter paper impregnated with 10% SDS, on a filter paper impregnated with 0.5M NaOH and 1.5M NaCl, and on a filter paper impregnated with a solution of 0.5M Tris-HCl, pH 7.5, 1.5M NaCl, respectively, for 3 minutes each in this order, washed sufficiently with 2×SSC, and dried. DNA was fixed on the filter using UV transilluminator. After the filter is immersed in 5×SSC, prehybridization was effected at 65° C. for 2 hours in a mixture of 6×SSC, 5×Denhardt solution, and 0.5% SDS solution (hybridization solution). After the prehybridization solution was removed, a mixture of a hybridization solution which had been heated to 65° C. in advance and the probe DNA obtained above at 1000000 cpm/ml (after heated at 100° C. for 5 minutes followed by rapid quenching) was poured onto the filter, and shaken slowly at 65° C. for 20 hours to effect hybridization. The membranes were washed three times with 1×SSC and 0.1% SDS solution each for ten minutes, and further washed three times at 65° C. with 0.1×SSC and 0.1% SDS solution each for 20 minutes. After the washed membranes were allowed to dry, the membranes were subjected to autoradiography at −80° C. overnight, and 27 colonies which had been strongly hybridized with the labeled probe were selected. In the plasmid DNA of these, PCR product of about 650 bp was confirmed by PCR mentioned above. These plasmids were named pSAIP 1, 2, 3, 4, 5, 6, 7, 8, 9, 10, 11, 12, 13, 14, 15, 16, 17, 18, 19, 20, 21, 22, 23, 24, 25, 26, and 27. All of these contained DNA sequences estimated from the amino acid sequence of AIP, and thus are believed to contain AIP cDNA. Among these, pSAIP, which was believed to have almost complete length, wag subjected to dye terminator method by fluorescent-labeling of dideoxynucleotide to determine the entire DNA sequence of its open reading frame. The DNA sequence is shown in SEQ ID No. 2 of the attached sequence listing, and the amino acid sequence estimated from the DNA sequence is shown in SEQ ID No. 1 of the sequence listing.

It was found that the cDNA sequence and the amino acid sequence estimated therefrom include all of the sequences obtained by determination of the partial amino acid sequence of AIP and pCRaip001 inserts, and confirmed that the cDNA codes AIP. From the comparison with the N-terminal amino acids of matured AIP, it is believed that base 1–90 code the signal peptide, and base 91–1575 code the matured peptide of AIP. The estimated molecular weight of the polypeptide which is coded by the cDNA is 58668 daltons (55243 daltons if the portion expected to be the signal peptide is excluded), which is about 7500 daltons lower than the molecular weight of AIP purified from viscus of mackerels. AIP is a glycoprotein which is strongly adsorbed on Con A column, and its sugar chain is believed to amount to about 7500 daltons.

Example 5

The purified AIP prepared in Example 1 was mixed and reacted with L-lysine, poly-L-lysine, or poly-D-lysine, and examined with coloring reagents (peroxidase and o-phenylene diamine) for generation of hydrogen peroxide. As a result, the purified AIP was found to oxidize L-lysine to generate about 2800 μM of hydrogen peroxide. On the other hand, when poly-L-lysine or poly-D-lysine was mixed, only less than 20 μM of hydrogen peroxide was generated at most. Further, the purified AIP generates hydrogen peroxide when not only lysine but also leucin, phenylalanine, arginine, methionine, histidine, or the like is used as a substrate. Accordingly, the purified AIP is believed to catalyze aldehyde-generating reaction by oxidative deamination to generate hydrogen peroxide.

Next, in order to determine the relation between the hydrogen peroxide-generating reaction by the oxidative reaction and the apoptotic activity of the purified AIP on cancer cells, the apoptotic activity of the purified AIP on cancer cells was examined with and without addition of catalase for catalyzing the decomposition of hydrogen peroxide. The measurement was performed in the same way as in the method for as determining the apoptotic activity of the purified leukemia cell (human leukemia cell HL-60) killing substance in Example 3 except for addition of catalase, and the percentage of the dead cells after 16 hours was measured. As a result, the percentage of the cell death was 18% when catalase was added in addition to the purified AIP, as the same time the percentage of the dead cells was 100% when only the purified AIP was added.

Therefore, it is believed that the apoptotic activity of the purified AIP on cancer cells is at least partly attributed to the reaction to catalyze the aldehyde-generating reaction by the oxidative deamination to generate hydrogen peroxide.

In this regard, the purified AIP was subjected to motif analysis to search for the domain exhibiting changes similar to the typical change in absorption of the visible spectrum observed in flavoprotein. As a result, it was found that amino acids 61–89 in the amino acid sequence of SEQ ID No. 1 of the attached sequence listing are the flavin-bonding domain. Consequently, it was revealed that one of the amino acid sequences required for the reaction to catalyze the aldehyde-generating reaction by oxidative deamination to generate hydrogen peroxide was amino acids 61–89 of the sequence.

Figure 10:
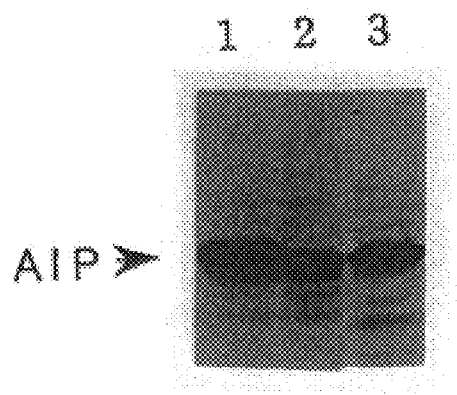
FIG. 10 is a photograph showing the results of Western blotting, using monoclonal antibodies prepared in Example 2, of mutant AIPs obtained by transfection with AIP gene and its mutants into African green monkey kidney cell line cos-7 in Example 5. Lane 1 represents complete AIP consisting of amino acids 1–524 Of SEQ ID No. 1, Lane 2 represents mutant AIP consisting of amino acids 1–496, and lane 3 represents mutant AIP consisting of amino acids 1–514.

Next, the AIP gene having the DNA sequence of SEQ ID No. 2 of the attached sequence listing was caused to vary by PCR method to obtain mutant genes, and plasmid obtained by constructing the mutant genes into an expression vector (pME18S) for mammal cells was transfected into a African green monkey kidney cell line cos-7 to prepare mutant AIPs each with amino acids 1–514 or 1–496, respectively, of SEQ ID No. 1 of the sequence listing. These mutant AIPs and the purified AIP obtained in Example 1 were subjected to Western blotting using the monoclonal antibodies prepared in Example 2. The results are shown in FIG. 10. Further, the apoptotic activity of the AIP and the mutant AIPs on human leukemia cells was determined in the same way as in Example 3. It was found that the complete AIP consisting of amino acids 1–524 and the mutant AIP consisting of amino acids 1–514 exhibited apoptotic activity on cancer cells, while the mutant AIP consisting of amino acids 1–496 has not apoptotic activity to be detected.

Consequently, it is understood that amino acids 497–514 of the sequence are also essential to maintain the function of AIP of the present invention.

Example 6

Figure 11:
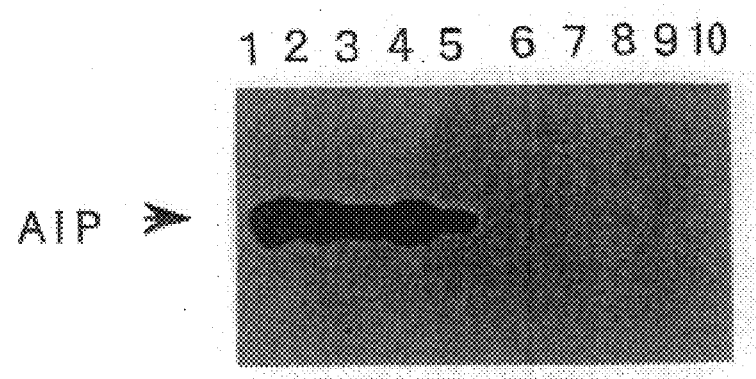
FIG. 11 is a photograph showing the results of Western blotting of extract of parasite-infected mackerel's viscus (Lanes 1–5) and of non-infected mackerel's viscus (Lanes 6–10) performed in Example 6, using the monoclonal antibodies prepared in Example 2.

In order to detect the origin of the purified AIP prepared in Example 1, the viscus of mackerels used were analyzed, which were found to be infected with parasites. Thus, extracts of viscera were prepared from 5 mackerels infected with parasites and from 5 mackerels not infected with parasites, in the same way as in Example 1. Each viscus extract thus obtained was subjected to Western blotting using the monoclonal antibodies prepared in Example 2. The results are shown in FIG. 11. In FIG. 11, Lanes 1–5 show the results of the viscus extracts from 5 mackerels infected with parasites, while Lanes 6–10 show the results of the viscus extracts from 5 mackerels not infected with parasites. Further, apoptotic activity of these viscus extracts on human leukemia cells was determined in the same way as in Example 3. The results are shown in Table 3. In Table 3, sample Nos. 1–5 show the results of the viscus extracts from 5 mackerels infected with parasites, while sample Nos. 6–10 show the results of the viscus extracts from 5 mackerels not infected with parasites. Further, the specific activity is indicated in relative values to the strength of the apoptotic activity of the viscus extract sample No. 5 on human leukemia cells, which is put as 1.

From the results in FIG. 11 and Table 3, the viscus extracts of the mackerels infected with parasites were found to contain AIP of the present invention, and to have apoptotic activity on cancer cells. On the contrary, the viscus extracts of the mackerels not infected with parasites were found to have no such activity. Therefore, it was revealed that the expression of AIP was induced in mackerels by infection with parasites.

From the above, it is decided that AIP is induced in mackerels by stimulation accompanied by activation of helper T2 cells (Th2 cells) such as infection with parasites, and that proteins having sequences homologous to AIP or having cell death inducing activity may be induced in mammals in the similar mechanism.

TABLE 3

| Sample No. | 1 | 2 | 3 | 4 | 5 | 6 | 7 | 8 | 9 | 10 |
|---|---|---|---|---|---|---|---|---|---|---|
| Specific Activity | 38 | 38 | 4 | 38 | 1 | 0 | 0 | 0 | 0 | 0 |

What is claimed is:

1. A protein comprising an amino acid sequence SEQ ID No. 1.

2. A protein according to claim 1, which protein has proliferation inhibitory activity on cancer cells, or cell death indicing activity.

3. A protein comprising amion acids sequence homologous to said amino acid sequence of SEQ ID No. 1 of sequence listing, and having proliferation inhibitory activity on cancer cells or cell death including activity.

4. A protein comprising amino acids 61–89 and 497–514 of SEQ ID No. 1 of said sequence listing, and having proliferation inhibitory activity on cancer cells or cell death inducing activity.

5. An isolated nucleic acid comprising a nucleotide sequence selected from the group consisting of:

(a) SEQ ID NO. 2: and (b) a nucleotide sequence homologous or analogous to SEQ ID No. 2 encoding a polypeptide having proliferation inhibitory activity on cancer cells or cell death inducing activity.

6. An isolated nucleic acid having an open reading frame that encodes the amino acid sequence set forth in SEQ ID NO: 1.

* * * * *

SEQUENCE LISTING

<160> NUMBER OF SEQ ID NOS: 2

<210> SEQ ID NO 1
<211> LENGTH: 524
<212> TYPE: PRT
<213> ORGANISM: Scomber japonicus

<400> SEQUENCE: 1

```
Met Asn Leu His Val Val Lys Trp Lys Leu Ser Val Val Ser Val Leu
 1               5                  10                  15

Ile Thr Leu Tyr Tyr Ser His Thr Val Ala Leu Ser Leu Lys Glu His
                20                  25                  30

Leu Ala Asp Cys Leu Glu Asp Lys Asp Tyr Asp Thr Leu Leu Gln Thr
            35                  40                  45

Leu Asp Asn Gly Leu Pro His Ile Asn Thr Ser His His Val Val Ile
        50                  55                  60

Val Gly Ala Gly Met Ala Gly Leu Thr Ala Ala Lys Leu Leu Gln Asp
 65                 70                  75                  80

Ala Gly His Thr Val Thr Ile Leu Glu Ala Asn Asp Arg Val Gly Gly
                85                  90                  95

Arg Val Glu Thr Tyr Arg Asn Glu Lys Glu Gly Trp Tyr Ala Glu Met
            100                 105                 110

Gly Ala Met Arg Ile Pro Ser Ser His Arg Ile Val Gln Trp Phe Val
        115                 120                 125

Lys Lys Leu Gly Val Glu Met Asn Glu Phe Val Met Thr Asp Asp Asn
130                 135                 140

Thr Phe Tyr Leu Val Asn Gly Val Arg Glu Arg Thr Tyr Val Val Gln
145                 150                 155                 160

Glu Asn Pro Asp Val Leu Lys Tyr Asn Val Ser Glu Ser Glu Lys Gly
                165                 170                 175

Ile Ser Ala Asp Asp Leu Leu Asp Arg Ala Leu Gln Lys Val Lys Glu
            180                 185                 190

Glu Val Glu Ala Asn Gly Cys Lys Ala Ala Leu Glu Lys Tyr Asp Arg
        195                 200                 205

Tyr Ser Val Lys Glu Tyr Leu Lys Glu Glu Gly Gly Leu Ser Pro Gly
210                 215                 220

Ala Val Arg Met Ile Gly Asp Leu Leu Asn Glu Gln Ser Leu Met Tyr
225                 230                 235                 240

Thr Ala Leu Ser Glu Met Ile Tyr Asp Gln Ala Asp Val Asn Asp Ser
                245                 250                 255

Val Thr Tyr His Glu Val Thr Gly Gly Ser Asp Leu Leu Pro Glu Ala
            260                 265                 270

Phe Leu Ser Val Leu Asp Val Pro Ile Leu Leu Asn Ser Lys Val Lys
        275                 280                 285
```

```
His Ile Arg Gln Ser Asp Lys Gly Val Ile Val Ser Tyr Gln Thr Gly
    290                 295                 300

Asn Glu Ser Ser Leu Met Asp Leu Ser Ala Asp Ile Val Leu Val Thr
305                 310                 315                 320

Thr Thr Ala Lys Ala Ala Leu Phe Ile Asp Phe Asp Pro Pro Leu Ser
                325                 330                 335

Ile Ser Lys Met Glu Ala Leu Arg Ser Val His Tyr Asp Ser Ser Thr
                340                 345                 350

Lys Ile Leu Leu Thr Phe Arg Asp Lys Phe Trp Glu Asp Asp Gly Ile
                355                 360                 365

Arg Gly Gly Lys Ser Ile Thr Asp Gly Pro Ser Arg Tyr Ile Tyr Tyr
    370                 375                 380

Pro Ser His Ser Phe His Thr Asn Glu Thr Ile Gly Val Leu Leu Ala
385                 390                 395                 400

Ser Tyr Thr Trp Ser Asp Glu Ser Leu Leu Phe Leu Gly Ala Ser Asp
                405                 410                 415

Glu Glu Leu Lys Glu Leu Ala Leu Arg Asp Leu Ala Lys Ile His Gly
                420                 425                 430

Glu Gln Val Trp Asp Lys Cys Thr Gly Val Ile Val Lys Lys Trp Ser
                435                 440                 445

Ala Asp Pro Tyr Ser Leu Gly Ala Phe Ala Leu Phe Thr Pro Tyr Gln
    450                 455                 460

His Leu Glu Tyr Ala Gln Glu Leu Phe Ser Ser Glu Gly Arg Val His
465                 470                 475                 480

Phe Ala Gly Glu His Thr Ala Phe Pro His Ala Trp Ile Glu Thr Ser
                485                 490                 495

Met Lys Ser Ala Ile Arg Ala Ala Thr Asn Ile Asn Lys Val Ala Asn
                500                 505                 510

Glu Glu Ser Thr Ile Glu His Thr Lys Asp Glu Leu
                515                 520

<210> SEQ ID NO 2
<211> LENGTH: 1575
<212> TYPE: DNA
<213> ORGANISM: Scomber japonicus

<400> SEQUENCE: 2
atgaatctgc atgtggtgaa atggaaatta tctgttgtca gtgtgctgat cacattgtac    60
tacagtcaca ctgttgctct cagcctgaag gaacatctgg ctgattgtct tgaagacaaa   120
gactatgaca cgctgctgca gactctggat aacggtcttc cacacattaa acgtctcat   180 catgtggtta tagtcggagc tggcatggcc ggactgacgg cggccaagtt actgcaagac   240
gcaggacaca cggtaaccat attggaggct aatgatcgtg ttggaggacg tgtggagacc   300
tacaggaatg aaaagaagg ctggtatgct gaaatgggag ctatgaggat cccaagctct   360
caccgcatcg tccagtggtt tgtcaaaaag cttgggggtcg agatgaatga gttcgtcatg   420
actgatgaca cacctttta cctggttaat ggggtgcggg agaggacata tgttgttcaa   480 gaaaccctg atgtcctgaa gtacaacgtg tcagaaagcg agaagggaat ttcagccgat   540
gatctgctag atcgagcttt gcagaaggtg aaagaggaag tggaagcaaa tggttgtaaa   600
gctgcactgg aaaaatacga ccgctattct gtgaaggagt atctgaaaga agaaggtggt   660
ttgagtccag gagcagtgag gatgattgga gacctgctga tgaacagag cctcatgtac   720 acagcgctga gtgagatgat ctacgaccag gctgacgtca atgacagtgt cacgtatcat   780
```

```
gaagtgacgg gtggatcaga tcttcttccc gaagcttttc tttctgtcct ggatgtcccc    840
atcctcttaa actccaaagt caaacacatc aggcagtcag ataaaggtgt aatcgtgtca    900
taccagacag gcaatgagtc ctctttgatg gacctttctg ctgacattgt tctggtaaca    960
accacagcca aagcagccct cttcatagac tttgatccac ctctctccat cagtaagatg   1020
gaggccctcc ggtcagtcca ctatgacagc tccactaaaa tcctcctcac ctttcgcgat   1080
aagttctggg aggacgatgg catccgagga ggcaagagca ttaccgatgg accttctcgt   1140
tacatctact atcccagcca cagtttccat acaaatgaga ccattggagt cctcctggca   1200
tcctacactt ggtctgacga gtccctcctc ttcctgggtg caagcgatga agagctgaaa   1260
gagctggccc tgagagatct ggcaaaaatc cacggtgagc aagtctggga taagtgcacg   1320
ggagtcatag tgaagaagtg gagcgctgat ccttacagct tgggcgcctt cgctctcttc   1380
acacctacc aacacttgga gtacgctcag gagctcttca gcagcgaggg cagggtgcac   1440
tttgctggtg aacacacagc cttccctcat gcttggatcg aaacgtctat gaaatctgca   1500
atcagggctg ctacaaatat taataaagtg gcaaatgaag agtcaactat agaacataca   1560
aaagatgagc tgtag                                                    1575
```